US012042209B2

(12) United States Patent
Lath et al.

(10) Patent No.: US 12,042,209 B2
(45) Date of Patent: Jul. 23, 2024

(54) INSERT GUIDE MEMBERS FOR SURGICAL INSTRUMENTS, AND RELATED DEVICES, SYSTEMS, AND METHODS

(71) Applicant: INTUITIVE SURGICAL OPERATIONS, INC., Sunnyvale, CA (US)

(72) Inventors: Adrit Lath, Mountain View, CA (US); Adam J. Ross, Prospect, CT (US); Robert C. Reid, Fairfield, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 690 days.

(21) Appl. No.: 16/872,538

(22) Filed: May 12, 2020

(65) Prior Publication Data
US 2020/0360078 A1 Nov. 19, 2020

Related U.S. Application Data
(60) Provisional application No. 62/848,618, filed on May 16, 2019.

(51) Int. Cl.
*A61B 18/14* (2006.01)
*A61B 34/35* (2016.01)
(Continued)

(52) U.S. Cl.
CPC .......... *A61B 18/1442* (2013.01); *A61B 34/35* (2016.02); *A61B 34/37* (2016.02);
(Continued)

(58) Field of Classification Search
CPC ...... A61B 18/1442; A61B 2018/00071; A61B 2018/00577; A61B 2018/0063;
(Continued)

(56) References Cited

U.S. PATENT DOCUMENTS

| 6,249,708 B1 * | 6/2001 | Nelson ................... A61N 1/056 607/122 |
| 7,090,637 B2 | 8/2006 | Danitz et al. |

(Continued)

FOREIGN PATENT DOCUMENTS

| CN | 101115418 A | 1/2008 |
| CN | 102098970 A | 6/2011 |

(Continued)

OTHER PUBLICATIONS

WS Hampshire, Inc., Material Data Sheet for Teflon Brand PTFE, Mar. 19, 2021, pp. 1.

(Continued)

*Primary Examiner* — Michael F Peffley
*Assistant Examiner* — Bo Ouyang
(74) *Attorney, Agent, or Firm* — JONES ROBB, PLLC (57) ABSTRACT

A surgical instrument includes a shaft, an end effector, and a wrist coupling the end effector to the shaft. The wrist has a central channel extending along a length of the wrist. An insert guide member is positioned in the central channel. The insert guide member has an exterior lateral wall extending between a first end and a second end of the insert guide member and an interior lateral wall extending between the first end and the second end. A passage extends from the first end of the insert guide member to the second end of the insert guide member. The passage can include a first portion extending through the insert guide member between an interior lateral wall of the insert guide member and the exterior lateral wall of the insert guide member, and a second portion intersecting the exterior lateral wall of the insert guide member.

20 Claims, 7 Drawing Sheets

(51) Int. Cl.
   *A61B 34/37* (2016.01)
   *A61B 18/00* (2006.01)
   *A61B 34/30* (2016.01)

(52) U.S. Cl.
   CPC ............ *A61B 2018/00071* (2013.01); *A61B 2018/00577* (2013.01); *A61B 2018/0063* (2013.01); *A61B 2018/1405* (2013.01); *A61B 2034/306* (2016.02)

(58) Field of Classification Search
   CPC . A61B 2018/1405; A61B 34/35; A61B 34/37; A61B 2034/306
   See application file for complete search history.

(56) References Cited

U.S. PATENT DOCUMENTS

| | | | |
|---|---|---|---|
| 7,130,700 | B2 | 10/2006 | Gardeski et al. |
| 7,320,700 | B2 | 1/2008 | Cooper et al. |
| 7,608,083 | B2 | 10/2009 | Lee et al. |
| 7,666,191 | B2 | 2/2010 | Orban, III et al. |
| 7,785,252 | B2 | 8/2010 | Danitz et al. |
| 7,819,884 | B2 * | 10/2010 | Lee .................. A61B 34/37 600/114 |
| 7,942,868 | B2 | 5/2011 | Cooper et al. |
| 8,545,515 | B2 | 10/2013 | Prisco et al. |
| 10,285,763 | B2 | 5/2019 | Vale et al. |
| 10,524,870 | B2 | 1/2020 | Saraliev et al. |
| 11,272,994 | B2 | 3/2022 | Saraliev et al. |
| 2003/0097128 | A1 | 5/2003 | Hayzelden |
| 2004/0167595 | A1 | 8/2004 | Tuominen |
| 2005/0015113 | A1 | 1/2005 | Baptiste et al. |
| 2006/0041293 | A1 | 2/2006 | Mehdizadeh et al. |
| 2006/0094931 | A1 | 5/2006 | Danitz et al. |
| 2006/0129171 | A1 | 6/2006 | Moskovich |
| 2007/0112355 | A1 | 5/2007 | Salahieh et al. |
| 2008/0065105 | A1 | 3/2008 | Larkin et al. |
| 2008/0099420 | A1 | 5/2008 | Shiue |
| 2008/0243176 | A1 | 10/2008 | Weitzner et al. |
| 2009/0088772 | A1 | 4/2009 | Blumenkranz |
| 2009/0191974 | A1 | 7/2009 | Weissenbock et al. |
| 2009/0206140 | A1 | 8/2009 | Scheib et al. |
| 2009/0306604 | A1 | 12/2009 | Darmos et al. |
| 2010/0042097 | A1 * | 2/2010 | Newton ............ A61B 18/1445 606/41 |
| 2010/0168717 | A1 | 7/2010 | Grasse et al. |
| 2010/0222677 | A1 | 9/2010 | Placek et al. |
| 2011/0009863 | A1 | 1/2011 | Marczyk et al. |
| 2011/0118755 | A1 | 5/2011 | Cooper et al. |
| 2011/0196419 | A1 | 8/2011 | Cooper |
| 2011/0277579 | A1 | 11/2011 | Anderson et al. |
| 2012/0215220 | A1 * | 8/2012 | Manzo .................. A61B 34/30 606/46 |
| 2012/0277762 | A1 | 11/2012 | Lathrop et al. |
| 2012/0310221 | A1 | 12/2012 | Durant et al. |
| 2012/0310254 | A1 | 12/2012 | Manzo et al. |
| 2013/0012928 | A1 * | 1/2013 | Cooper .............. A61B 17/062 606/1 |
| 2013/0184686 | A1 | 7/2013 | Sandford et al. |
| 2013/0325031 | A1 | 12/2013 | Schena et al. |
| 2013/0325033 | A1 | 12/2013 | Schena et al. |
| 2013/0340559 | A1 | 12/2013 | Danitz et al. |
| 2013/0345679 | A1 | 12/2013 | Garon et al. |
| 2014/0296869 | A1 | 10/2014 | Kernbaum et al. |
| 2016/0067450 | A1 | 3/2016 | Kowshik |
| 2016/0089213 | A1 | 3/2016 | Crews et al. |
| 2019/0231457 | A1 | 8/2019 | Vale et al. |
| 2019/0314098 | A1 | 10/2019 | Park et al. |
| 2020/0170734 | A1 | 6/2020 | Saraliev et al. |

FOREIGN PATENT DOCUMENTS

| | | |
|---|---|---|
| CN | 101507634 B | 10/2012 |
| DE | 2820239 A1 | 11/1978 |
| EP | 0165718 A2 | 12/1985 |
| EP | 3085324 A1 | 10/2016 |
| JP | S53139390 A | 12/1978 |
| JP | S6449533 A | 2/1989 |
| JP | H10176810 A | 6/1998 |
| JP | 2004337994 A | 12/2004 |
| JP | 2006506195 A | 2/2006 |
| JP | 2009165504 A | 7/2009 |
| JP | 2010501319 A | 1/2010 |
| JP | 2011206268 A | 10/2011 |
| WO | WO-2004052171 A2 | 6/2004 |
| WO | WO-2005120326 A2 | 12/2005 |
| WO | WO-2009151958 A2 | 12/2009 |
| WO | WO-2011097095 A1 | 8/2011 |
| WO | WO-2015061674 A1 | 4/2015 |
| WO | WO-2015127231 A1 | 8/2015 |
| WO | WO-2015127250 A1 | 8/2015 |

OTHER PUBLICATIONS

Extended European Search Report for Application No. 15752254.1, mailed on Jun. 9, 2017, 10 pages.
Extended European Search Report for Application No. EP15773899.8, mailed on Nov. 7, 2017, 10 pages.
International Search Report and Written Opinion for Application No. PCT/US15/16854, mailed on May 27, 2015, 17 pages.
International Search Report and Written Opinion for Application No. PCT/US15/20914, mailed on Jun. 9, 2015, 12 pages.
Office Action mailed Jul. 27, 2018 for Chinese Application No. 201580009399.2 filed Feb. 20, 2015, 24 pages.
Office Action mailed Jan. 3, 2020 for Chinese Application No. 2015817379 filed Mar. 17, 2015, 26 pages.
Salle D., et al., "Surgery Grippers for Minimally Invasive Heart Surgery," Proceeding of IEEE International Conference on Intelligent Manipulation and Grasping (IMG 04), Jul. 2004, 8 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INSERT GUIDE MEMBERS FOR SURGICAL INSTRUMENTS, AND RELATED DEVICES, SYSTEMS, AND METHODS

CROSS-REFERENCE TO RELATED APPLICATIONS

This application claims priority to U.S. Provisional Application No. 62/848,618 (filed May 16, 2019) entitled "Insert Guide Members for Surgical Instruments, and Related Devices, Systems, and Methods," the entire contents of which are incorporated by reference herein.

TECHNICAL FIELD

Aspects of the present disclosure relate to devices, systems and methods for routing actuation members in surgical instruments.

INTRODUCTION

Surgical instruments can have a variety of configurations to perform various types of surgical procedures.

Some surgical instruments are configured for minimally invasive surgery, and include various components, such as one or more actuation members used for remotely controlling movement of the instrument. Such actuation members can have a variety of forms, such as wires, cables, rods, and other force transmission members. They can be used in combination with various drives, pulleys, etc. to transmit force from an input at one end of the instrument, along the instrument shaft, and to a moveable component, such as an end effector and/or one or more joints (e.g., wrist members) located toward a distal portion of the instrument. In addition to one or more actuation members, some surgical instruments also may have one or more flux conduits routed along the shaft to the end effector. For example, in electrosurgical instruments that are configured to provide electrical energy to ablate, fulgurate, fuse, blend, seal, etc. tissue, one or more electrical conductors in communication with an energy source are routed along the instrument. Other flux conduits may include tubes for transporting gasses or liquids (such as may be used for irrigation or evacuation) or conduits for delivering light energy (such as lasers or optical fibers). In instruments designed for minimally invasive applications, space issues arise due to the need to route multiple such actuation members and/or flux conduits through the instrument. Space issues may be compounded when having to route such components through instruments that have one or more joints. Moreover, routing actuation members and/or flux conduits through instruments may pose issues relating to undesirable constraint of movement of the instrument and/or undesirable stress/strain induced in the actuation members and/or flux conduits as a result of movement of the various components, including a joint or shaft, of an instrument.

There exists a need to provide surgical instruments in which multiple actuation members and/or flux conduits are supported and routed through an instrument, including, for example, through one or more joints of the instrument, in a manner that contributes to reliability and ease of manufacturing. There also exists a need to provide routing and housing of the various actuation members and/or flux conduits that may be part of an instrument, for example to minimize damage to the instrument, including the actuation members and/or flux conduits. For example, there is a need to route the flux conduits in a manner that minimizes length change through the one or more joints during articulation of the joints, to protect the conduits from being pinched by joint members during articulation, and resist buckling and/or stretching and provide column strength to actuation members. Additionally, in instruments in which the flux conduits are electrical conductors, there is a need to keep the flux conduits spaced away from other instrument components, such as an electrically conductive main shaft, to avoid capacitive coupling.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument includes a shaft, an end effector, and a wrist coupling the end effector to the shaft. The wrist has a central channel extending along a length of the wrist. An insert guide member is positioned in the central channel. The insert guide member has an exterior lateral wall extending between a first end and a second end of the insert guide member and an interior lateral wall extending between the first end and the second end. The interior lateral wall defines a bore. A passage extends from the first end of the insert guide member to the second end of the insert guide member. The passage can include a first portion extending through the insert guide member between an interior lateral wall of the insert guide member and the exterior lateral wall of the insert guide member, and a second portion intersecting the exterior lateral wall of the insert guide member.

In accordance with at least another exemplary embodiment, a surgical instrument includes a shaft, an end effector, and a wrist coupling the end effector to the shaft, the wrist having a central channel extending along a length of the wrist through a first end portion and a second end portion of the wrist. An insert guide member is positioned in the central channel. The insert guide member includes an exterior lateral wall extending between a first end and a second end of the insert guide member and an interior lateral wall extending between the first end and the second end. The interior lateral wall defines a bore. A passage intersects the exterior lateral wall of the insert guide member, and at least a first portion of the passage follows a non-helical path along the wrist.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification.

The drawings illustrate one or more exemplary embodiments of the present teachings and, together with the description, explain certain principles and operation. In the drawings.

DETAILED DESCRIPTION

The present disclosure contemplates various exemplary embodiments of insert guide members for surgical instruments that are configured to route actuation members and/or flux conduits through wrist mechanisms of surgical instruments. Insert guide members according to various embodiments of the present disclosure can include various features configured to facilitate manufacturability of the insert guide member, which may also contribute to a relatively low overall cost of making the instrument. Moreover, various embodiment of the present disclosure can minimize the risk of damage caused by stress and/or strain of the actuation members and/or flux conduits. Further, various embodiments of the present disclosure can route actuation members and/or flux conduits in a manner to allow proper movement of the instrument without undue constraint.

For example, insert guide members of the present disclosure can include passages for flux conduits and/or actuation members that pass through articulatable wrist portions of the instrument, and the passages can be configured such that the length of the passages is conserved or minimized to a level such that the flux conduits are not subject to undue strain as the wrist portions articulate. Such passages can be formed in an exterior lateral wall of the insert guide member, thereby facilitating access to the passage for machining operations and/or simplifying mold design and configuration for injection molding. Further, while the passages can be configured to have an angular displacement as they extend from one portion of the insert guide member to another portion of the insert guide member, the passages can be formed along a spline path that lies within a plane and intersects, or nearly intersects, axes of articulation of the joints to further simplify design and manufacturing.

The insert guide member can include multiple portions formed integrally or formed separately and bonded together. For example, the insert guide member can include a proximal portion, an intermediate portion, and a distal portion. The proximal portion can be configured to be at least partially received within a shaft of the surgical instrument, the intermediate portion can be configured to be received within the wrist of the instrument, and the distal portion can be at least partially received within a component of an end effector of the instrument. Each of the portions of the insert guide member can include a portion of the passages. Optionally, only the portion of the passages extending through the intermediate portion are configured for length change minimization (e.g., substantial length conservation).

Exemplary embodiments of the present disclosure provide surgical instruments maintaining desired functionality while facilitating manufacturing.

Figure 1:
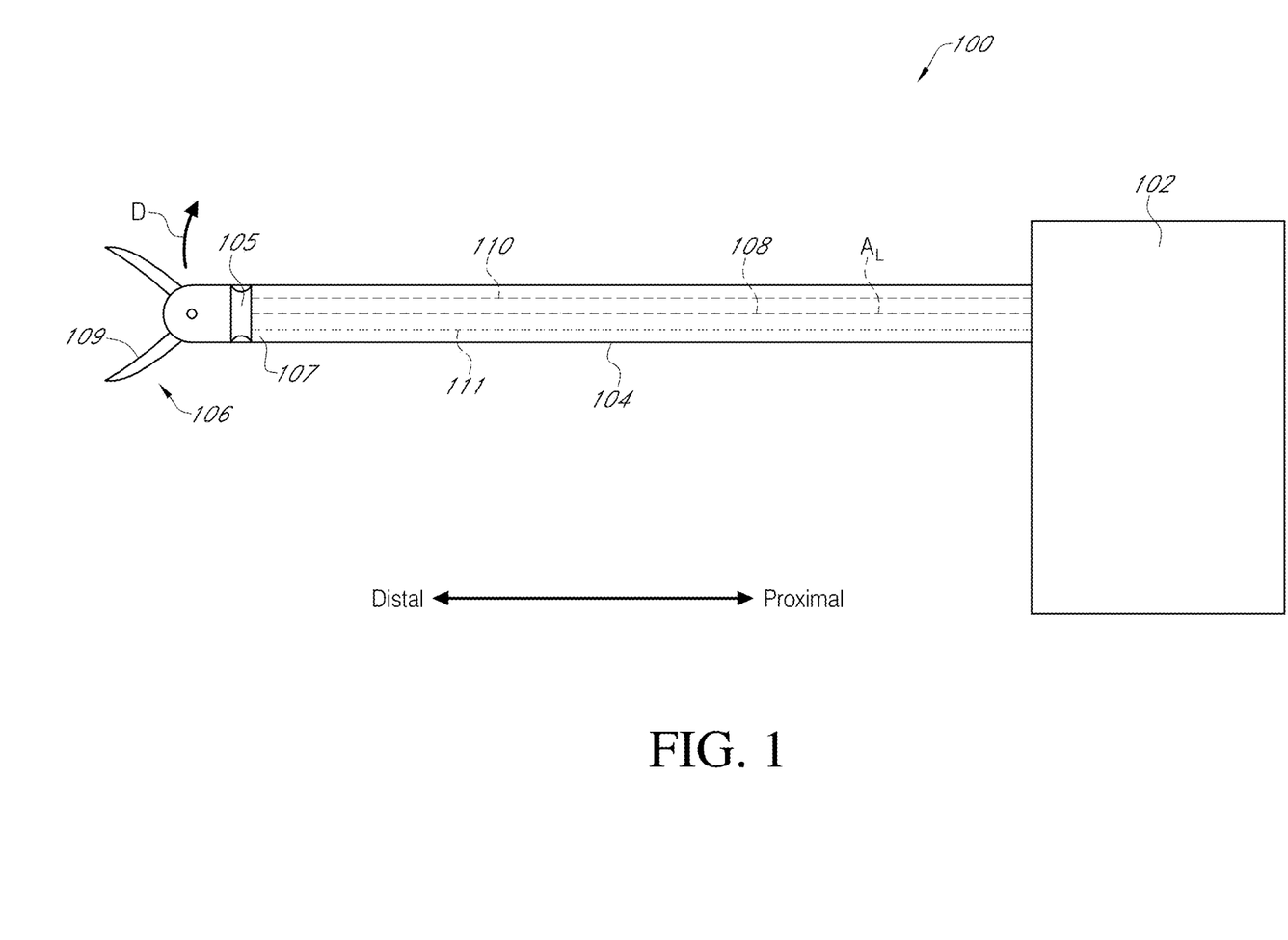
FIG. 1 is a schematic view of an embodiment of a surgical instrument according to an embodiment of the present disclosure.

Referring now to FIG. 1, a schematic side view of an embodiment of an instrument 100 (such as, for example, a surgical instrument) is shown. While aspects of the present disclosure are discussed in the context of surgical instruments, embodiments of the present disclosure can be used with various instruments used in surgical procedures. For example, such instruments include those used for diagnosis, therapy, and sensing, including, for example, imaging instruments such as endoscopes and other imaging instruments. Accordingly, the term "surgical instrument" as used herein encompasses a variety of instruments used in surgical, diagnostic, and therapeutic applications. In addition, aspects of the disclosure can have non-surgical applications, such as in other remotely-actuatable instruments for inspection and other industrial uses, general robotic uses, manipulation of non-tissue work pieces, etc. The instrument 100 includes a transmission mechanism 102. In an exemplary embodiment, the transmission mechanism 102 is configured to interface with a manipulating system, such as manipulating systems shown below in connection with FIGS. 5 and 6, respectively. Alternatively, the transmission mechanism 102 can be configured to be operated manually such as for a manual, laparoscopic instrument. A shaft 104 extends distally from the transmission mechanism 102. An end effector 106 is coupled to the distal end portion of the shaft 104. The end effector can be coupled directly to the shaft 104 or may be coupled to the shaft 104 by a wrist 105, which may include one or more articulatable joints to impart one of more degrees of freedom of movement to the end effector 106 relative to the shaft 104 (for example, to move the wrist in one or more of pitch and yaw).

Figure 5:
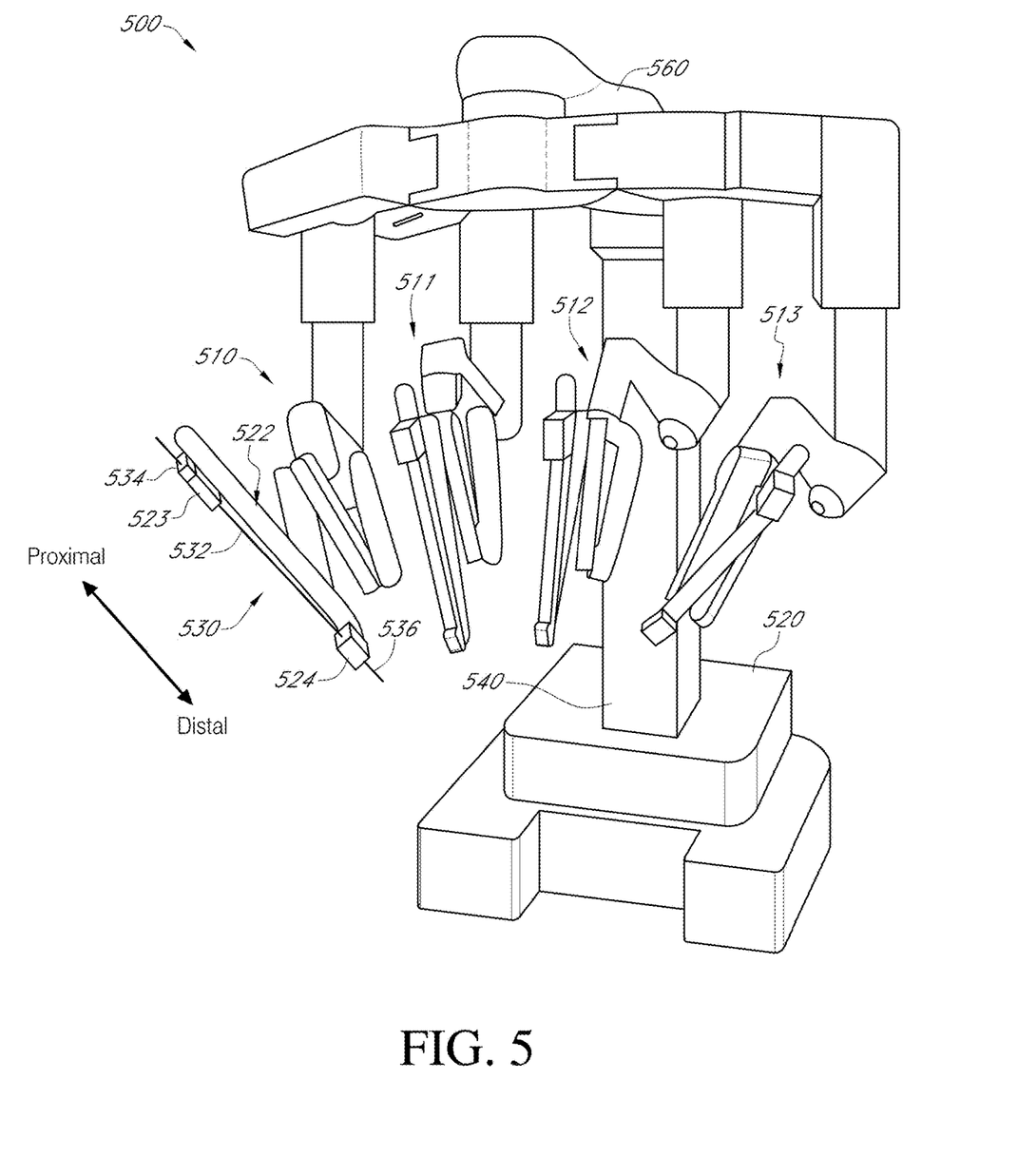
FIG. 5 is a perspective view of a manipulating system according to an embodiment of the present disclosure.
Figure 6:
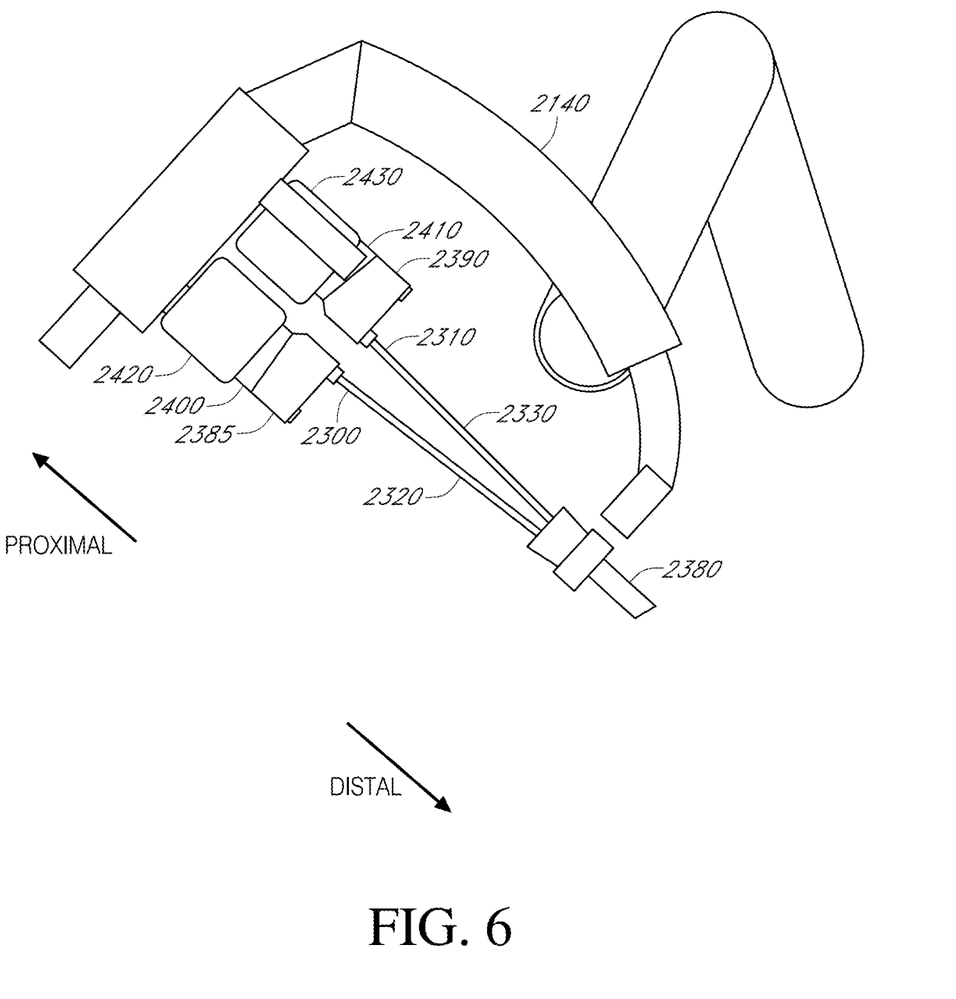
FIG. 6 is a partial schematic view of an embodiment of a manipulator arm of a manipulating system according to the present disclosure with two instruments in an installed position.

Operation of the end effector 106 can be controlled by manipulation of the transmission mechanism 102, either manually or through drives of a manipulating system (e.g., the manipulating systems shown in FIGS. 5 and 6). The transmission mechanism 102 includes various mechanical and/or electromechanical devices that transmit motion, energy, and/or signals, e.g., from the manipulating system, or from inputs at the transmission mechanism 102 operable by a user, to the end effector 106. For example, one or more actuation members (one actuation member 108 shown in FIG. 1) can extend from the transmission mechanism 102, through the shaft 104, and to the end effector 106, so as to operably couple the transmission mechanism 102 (or a component therein) to the end effector 106. Force applied to the actuation member 108 by the transmission mechanism 102 can actuate (e.g., close, open, or otherwise control) the end effector 106. While the end effector 106 shown in FIG. 1 comprises a pair of opposing jaw members, other end effector configurations, such as staplers, clip appliers, ligation tools, and other tools are considered within the scope of this disclosure.

As noted above, the instrument 100 may also include the wrist 105 to facilitate orienting the end effector 106. For example, the wrist 105 may comprise one or more articulating joints disposed at a distal end portion 107 of the shaft 104 and couple the end effector 106 to the shaft 104 so that the end effector 106 moves relative to the shaft in one or more degrees of freedom. Accordingly, the actuation member 108 may be configured to bend with the wrist 105 (e.g., by elastic deformation) during articulation of the wrist 105 from a neutral position relative to the shaft 104. The actuation member 108 may comprise a metal material, a polymer material, a composite material, or some other material capable of deflecting during articulation of the wrist 105. As a non-limiting example, the actuation member 108 may comprise a tungsten cable, and may be solid, stranded, braided, etc. The actuation member 108 may be configured as a "push/pull" member. In other words, the actuation member 108 may be configured to transfer tensile and compressive forces placed on the actuation member 108 by the transmission mechanism 102 to the end effector 106 to operate (e.g., open or close jaws of) the end effector 106. For example, the actuation member 108 may translate alternately in the distal and proximal directions (shown in FIG. 1) to operate the end effector 106.

The wrist 105 can optionally include multiple articulating joint mechanisms to provide the desired number of degrees of freedom of movement to the end effector 106. Certain coordinated movements of multiple joints can enable, for example, pivoting of the end effector 106, longitudinal translations, combined movement in pitch and yaw directions, or other compound movements of the end effector 106 in multiple degrees of freedom relative to the instrument shaft 104. While a single actuation member 108 is shown in connection with FIG. 1, other, additional actuation members may also be operably coupled between the transmission mechanism 102 and the wrist 105 to actuate articulation of the wrist 105 along various degrees of freedom associated with individual joints of the wrist 105.

In exemplary embodiments, one or more flux conduits 110, 111 also extend through the shaft 104, e.g., from the transmission mechanism 102 to the end effector 106. For example, in FIG. 1, the end effector 106 comprises an electrocautery tool, such as a monopolar or bipolar electrocautery tool. Accordingly, the end effector 106 can include one or more electrodes 109 on one or both jaws, or other end effector components, operable to deliver electrosurgical energy. In embodiments in which the end effector 106 is a bipolar tool, two electrical conductors (such as the flux conduits 110, 111) extend from the transmission mechanism 102 and connect to respective jaws of the end effector 106. Electrical energy may be conducted through the flux conduits 110, 111 and delivered to the end effector 106 to carry out electrosurgical operations such as, for example, cauterizing, fulgurating, sealing, fusing, blending, ablating, etc. The end effector can be configured as a bipolar instrument or a monopolar instrument. In other embodiments, flux conduits could include, for example, tubes for supplying insufflation gas and/or vacuum to a subject site, optical fibers for transmitting light or light signals, or other types of conduits.

The one or more flux conduits 110, 111 and the actuation member 108 pass through the wrist 105. To ensure proper operation of the end effector 106, the actuation member 108 must be supported along a longitudinal axis $A_L$ (co-located with the schematic depiction of the actuation member 108 in FIG. 1) of the shaft 104 and wrist 105 as the wrist 105 is articulated. Because the actuation member 108 is located along the longitudinal axis of the wrist 105, the flux conduits 110, 111 are required to be routed along a path radially offset from the longitudinal axis of the wrist 105. Accordingly, articulation of the wrist 105 could potentially induce tensile stress in the flux conduits 110, 111 due to a changing path length along which the flux conduits 110, 111 are routed. For example, in the embodiment of FIG. 1, if the wrist 105 were articulated in a direction D in the view of FIG. 1, the flux conduit 111 (below the centerline of the wrist 105) would be subjected to a tensile force, while the flux conduit 110 (above the centerline of the wrist 105) would become slack due to a decrease in path length.

To provide support for the actuation member 108 and to route the flux conduits 110 and 111 through the wrist 105, an insert guide member that passes through a central channel of the wrist 105 may be used. The insert guide member can include a central bore (which may comprise a circular or non-circular cross sectional shape) concentric with a longitudinal axis of the insert member and configured to receive and route the actuation member 108, and passages located toward a periphery that are configured to receive and route the flux conduits 110, 111 along a path that facilitates articulation of the wrist 105 without inducing significant stress or strain in the flux conduits 110, 111. For example, the passages of the insert guide member can be configured to route the flux conduits 110, 111 along a path that minimizes length change (e.g., substantially conserves length) of the passages as the wrist 105 is articulated.

Figure 2:
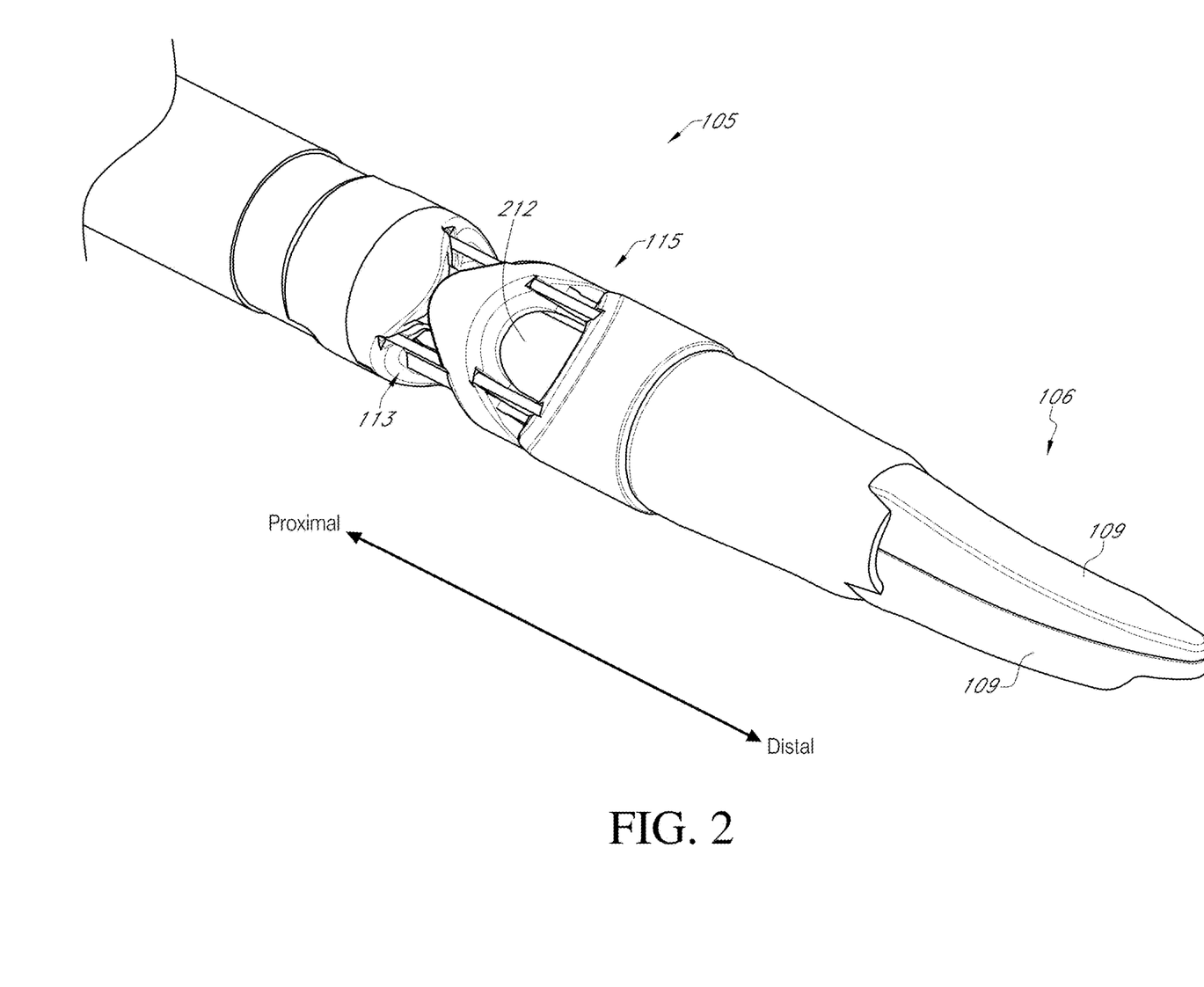
FIG. 2 is a perspective view of an embodiment of a surgical instrument according to an embodiment of the present disclosure.

Referring now to FIG. 2, an exemplary embodiment of a wrist 105 and end effector 106 according to the present disclosure are shown. The wrist 105 includes two joints 113 and 115 with axes of rotation orthogonal to one another, as will be discussed further in connection with FIG. 3A. Other numbers of joints, such as a single joint or three or more joints, and considered within the scope of this disclosure. An end effector 106 comprising opposing jaw members 109 is coupled at a distal end of the wrist 105. An insert guide member 212 as discussed in detail below in connection with FIG. 3A is shown passing through the wrist 105.

Figure 3A:
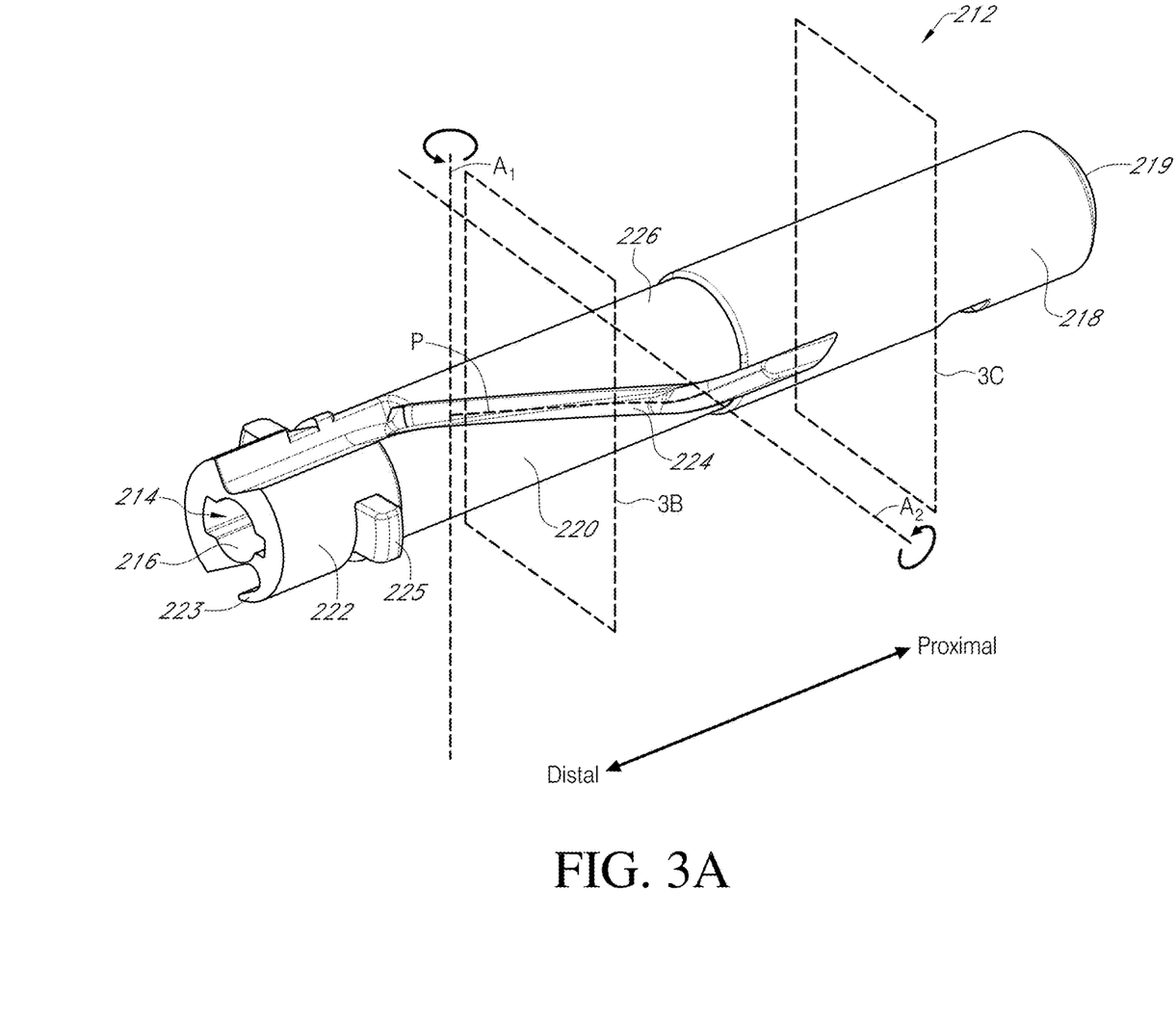
FIG. 3A is a perspective view of an insert guide member according to an embodiment of the present disclosure.

Referring now to FIG. 3A, an insert guide member 212 according to an embodiment of the disclosure is shown. The insert guide member 212 includes a central bore 214 defined by an interior lateral wall 216 and configured to receive an actuation member (such as actuation member 108 in FIG. 1) and route the actuation member along the centerline of the wrist 105 (FIG. 1). Maintaining the actuation member 108 along the longitudinal axis of the wrist 105 helps to ensure that tensile forces induced in the actuation member 108, e.g., by the transmission mechanism 102 (FIG. 1) are transferred to the end effector 106 to actuate the end effector without causing undesired articulation of the wrist 105. For example, if the actuation member 108 were offset from the centerline of the wrist 105, forces in the actuation member 108 could potentially cause articulation of the wrist 105 in an undesired manner. The central bore 214 provides lateral support for the actuation member 108 to prevent buckling of the actuation member 108 under compressive forces. In an exemplary embodiment, the diameter of the actuation member is on the order of several hundredths of an inch. For example, the diameter of the actuation member 108 is in a range of about 0.03" to about 0.06". In one embodiment, the diameter of the actuation member 108 is about 0.047". The diameter of the central bore 214 is larger than the diameter of the actuation member 108 by an amount ranging from about 0.005" to about 0.015" to provide clearance for the actuation member 108. The outer diameter of the insert guide member can be in a range of, for example, greater than 0.1" but less than 0.15", greater than 0.15" but less than 0.2", depending on the overall diameter of the instrument.

The insert guide member 212 can include multiple portions that extend through different components of the instrument 100 (FIG. 1). For example, the insert guide member 212 can include a proximal portion 218 configured to fit at least partially within the distal end portion 107 of the shaft 104 (FIG. 1) extending proximally from the wrist 105, an intermediate portion 220 configured to extend through the wrist 105 (FIG. 1), and a distal portion 222 configured to be located at least partially within a component of the end effector 106 (FIG. 1). The distal portion 222 can also include features configured to interface with components of the end effector, such as alignment ears 225 that are configured to be positioned within corresponding openings in the end effector 106 to maintain alignment of the insert guide member 212, as shown below in connection with FIG. 4. The proximal portion 218, intermediate portion 220, and distal portion 222 can be formed as a monolithic structure (i.e., as a single component). Alternatively, one or more of the proximal portion 218, the intermediate portion 220, and the distal portion 222 can be formed individually and bonded or otherwise coupled to one another so as to be integrally joined to produce the insert guide member. For example, the proximal portion 218, intermediate portion 220, and distal portion 222 could be formed separately and coupled to one another by adhesive bonding, laser welding, insert molding, or other processes or combinations of processes.

Figure 3B:
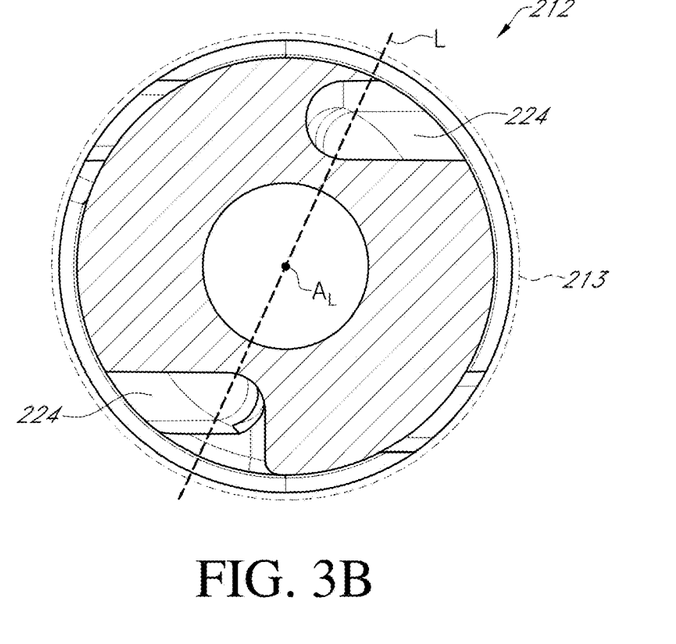
FIG. 3B is a cross-sectional view of the insert guide member according to the embodiment of FIG. 3A.
Figure 4:
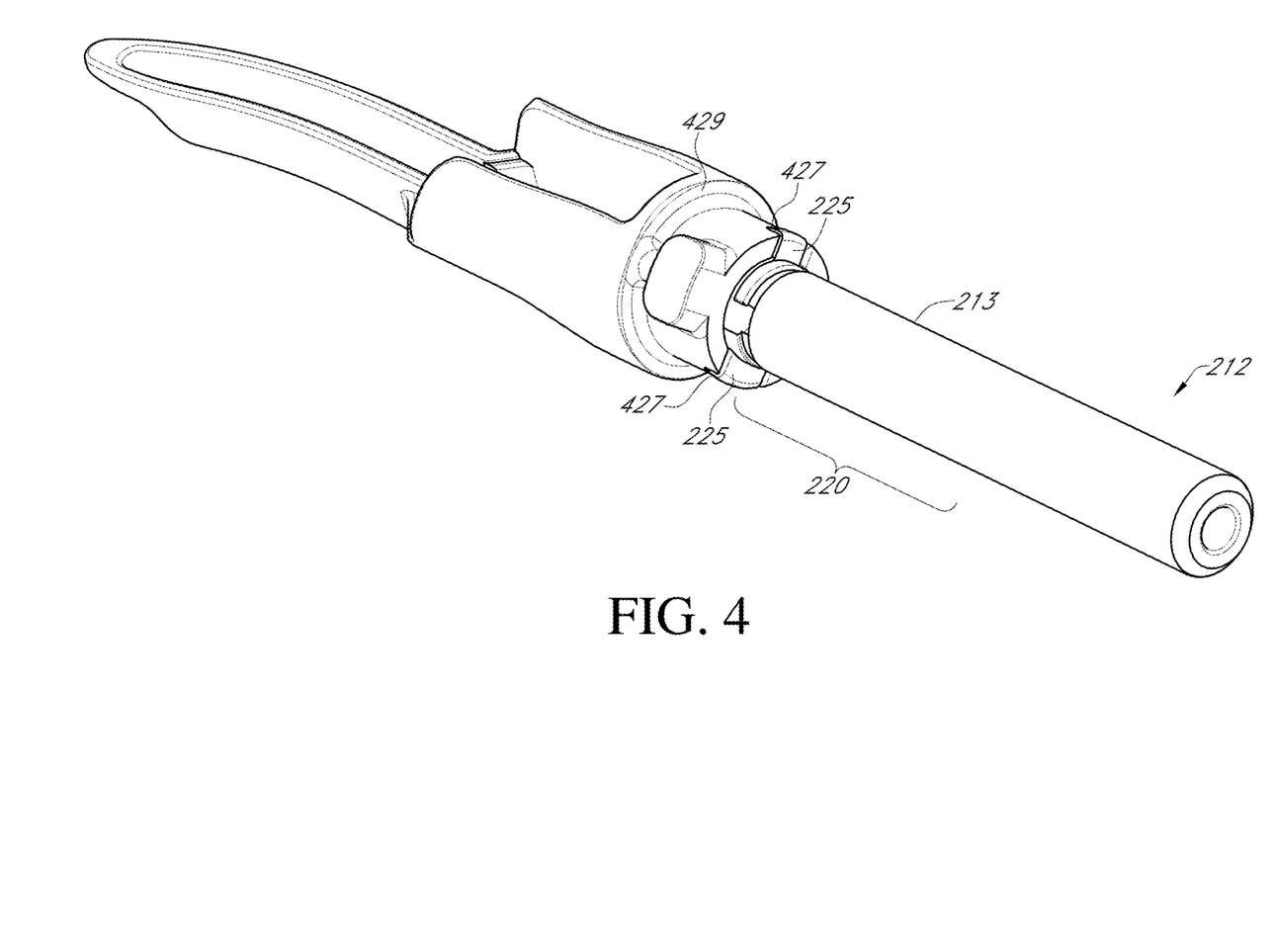
FIG. 4 is a partial perspective view of the insert guide member of FIG. 3A and a portion of an instrument according to the disclosure.

The intermediate portion 220 includes one or more passages configured to receive and route one or more flux conduits (such as flux conduits 110, 111 shown in FIG. 1) and route the flux conduits in such a way that length of the passages and flux conduits is minimized (e.g., substantially conserved) when the wrist 105 is articulated or otherwise in a bent configuration, as discussed in greater detail in connection with FIG. 4. For example, as shown in FIG. 3A, the intermediate portion 220 includes one or more passages 224 that are radially offset from the central bore 214. The one or more passages 224 can begin at a first circumferential location on the intermediate portion 220 adjacent the proximal portion 218 and end at a second circumferential location on the intermediate portion 220 adjacent the distal portion 222. While only one passage 224 is visible in FIG. 3, the embodiment of FIG. 3 includes two passages 224 opposite one another about the longitudinal axis $A_L$, as shown in cross-sectional views of FIGS. 3A and 3B discussed below. Insert guide members with a single passage, or insert guide members with three, four, or more passages are within the scope of this disclosure.

The passages 224 can be configured in various ways to facilitate manufacturing of the insert guide member 212. For ease of reference, the following description refers to the passages 224, but equally applies to as many such passages as are provided as part of the insert guide member. For example, the passages 224 can optionally be formed in an exterior lateral wall 226 (FIG. 3A) of the intermediate portion 220. Forming the passages 224 in the exterior lateral wall 226 can facilitate manufacturing by ensuring the passages 224 are accessible to tools used to form the insert guide member 212, such as molds for injection molding, cutting tools for machining, or other tools. The insert guide member 212 is optionally injection-molded, and the location of the passages 224 exposed in the exterior lateral wall 226 of the insert guide member 212 facilitates injection molding with a single mold, compared to other configurations, such as with passages formed on the interior lateral wall 216 or between the interior lateral wall 216 and exterior lateral wall 226 (i.e., passages formed in a thickness of an insert guide member), which may require molds that necessitate complex actions during manufacture of the insert member and thus increase complexity and cost of production. In some embodiments, the intermediate portion of the insert guide member 212 can be covered by a sleeve to ensure the flux conduits remain within the passages 224 and to prevent damage to the flux conduits by components of the wrist 105. For example, with brief reference to FIG. 3B, such a sleeve is indicated by dashed line 213. The sleeve 213 can comprise a material that is flexible and able to survive repeated articulations and elastomeric such that it can be stretched for assembly over the insert guide member 212 and remain in place once assembled. Referring now to FIG. 4, the sleeve 213 is shown installed over the insert guide member 212 and covering the intermediate portion 220 to protect flux conduits (not visible in FIG. 4) from damage. Also shown in FIG. 4 are alignment ears 225 received within alignment notches 427 formed in a portion (such as a jaw portion) 429 of an end effector (such as end effector 106 in FIG. 1).

With reference again to FIG. 3A, the passages 224 can extend continuously through the insert guide member 212 from a proximal face 219 of the proximal portion 218 to a distal face 223 of the distal portion 222. The passages 224 can extend through the proximal portion 218 between the interior lateral wall 216 and the exterior lateral wall 226. In other words, the passages 224 extend through a thickness of the proximal portion 218 without intersecting either the interior lateral wall 216 or the exterior lateral wall 226, as shown in cross-section in FIG. 3C and discussed below. Because the proximal portion 218 does not extend through the wrist 105 (FIG. 1), no angular displacement of the passages 224 is necessary for length conservation purposes, and the passages 224 can be formed along a line parallel with a centerline of the central bore 214. Thus, the passages 224 can be formed between the interior lateral wall 216 and exterior lateral wall 226 through the proximal portion 218 of the insert guide member without introducing unwanted complexity in manufacturing tooling. Positioning the passages 224 between the interior lateral wall 216 and the exterior lateral wall 226 in the proximal portion 218 can also facilitate sealing of interior of the shaft 104 (FIG. 1) from an environment in which the end effector 106 of the instrument 100 is used.

The cross-sectional shape of the passages 224 in the intermediate portion 220 may be chosen to provide adequate support for the actuation member 108 (FIG. 1). For example, referring now to FIG. 3B, a cross-section of the insert guide member 212 in the plane of 3A is shown. The cross-section is non-symmetrical about a line L perpendicular to the longitudinal axis $A_L$ of the insert guide member 212. When the actuation member 108 is placed under a compressive load, preventing buckling of the actuation member 108 requires supporting the actuation member 108 with a reaction force perpendicular to the longitudinal axis $A_L$. The non-symmetrical configuration of the cross section of the insert guide member 212 ensures that sufficient material remains in the insert guide member 212 along line L in any rotational orientation about the longitudinal axis $A_L$ to adequately support and prevent buckling of the actuation member 108.

Figure 3C:
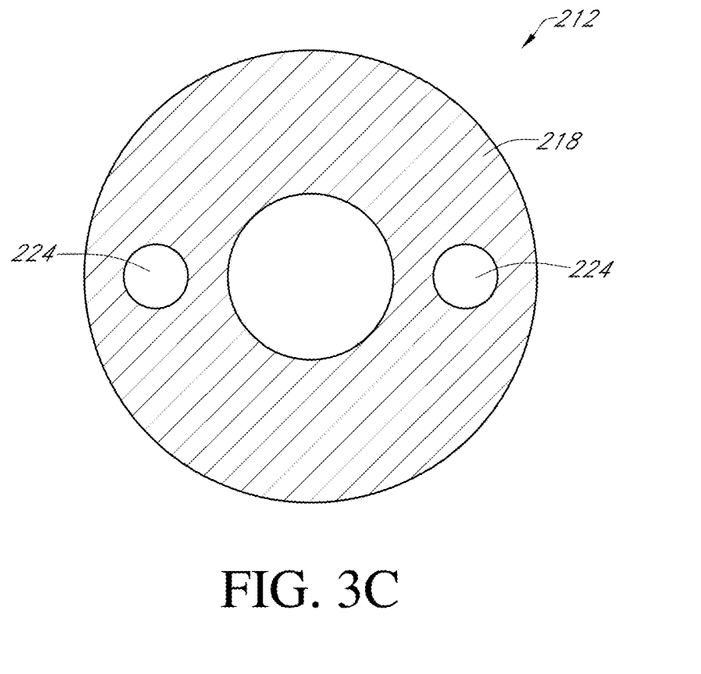
FIG. 3C is another cross-sectional view of the insert guide member according to the embodiment of FIG. 3A.

Referring now to FIG. 3C, a transverse cross-section of the proximal portion 218 of the insert guide member 212 in plane 3C (FIG. 3) is shown. As discussed above, the passages 224 are formed between the interior lateral wall 216 and the exterior lateral wall 226. Because the proximal portion 218 is not subjected to articulation of the wrist 105, the passages 224 can be formed parallel to the longitudinal axis $A_L$. The longitudinally parallel nature of the passages 224 enables forming the passages between the interior and exterior walls (i.e., not intersecting either the interior or exterior lateral walls) without causing undue manufacturing challenges. Further, as noted above, forming the passages 224 between the interior and exterior lateral walls can also facilitate sealing the flux conduits (e.g., 110, 111 in FIG. 1) within the passages 224 to seal the interior of the shaft 104 from the environment to which the end effector 106 and wrist 105 are exposed.

At locations where the passages 224 extend over the intermediate portion 220 of the insert guide member 212, the passages 224 can include additional features or configurations to facilitate manufacturing. For example, the passages 224 may follow a non-helical path as they extend along the longitudinal axis of the insert guide member 212. Referring again to FIG. 3A, passages 224 (one being shown in FIG. 3A but applies to both passages 224) follow a path P as they extend from the proximal portion 218 to the distal portion 222. Dashed lines $A_1$ and $A_2$ represent axes of two joints forming a wrist (e.g., joints 113 and 115 in FIG. 2) and are orthogonal to one another. Without wishing to be bound by any particular theory, the inventors have determined that the particular shape of the path P is not required to be a helix, and non-helical shapes provide acceptable length change minimization (e.g., substantial length conservation) as long as the path P intersects or nearly intersects both axes $A_1$ and $A_2$. As one possible approach to forming the path P as a shape simplified from a true helix, a plane normal to one of axes $A_1$ or $A_2$ can be chosen and the projection of the path P can be formed as a spline lying in the chosen plane. The projection of the path P, as it lies in the plane, is then chosen such that it intersects, or nearly intersects, the other of axis $A_1$ or $A_2$ as viewed within the chosen plane. Any projection of the spline path P within the plane can be chosen as long as the projection of the path P intersects or nearly intersects the axes $A_1$ and $A_2$. For example, as shown in FIG. 3A, if a plane normal to $A_2$ were chosen, the path P, as projected onto the plane normal to $A_2$, would pass through, or nearly pass through, axis $A_2$. In some exemplary embodiments, the projection of the path within the plane can optionally be linear. Configuring the passages 224 in this manner can further simplify design and manufacturing, and correspondingly reduce production costs of the insert guide member 212. In other embodiments, the passages 224 can optionally be formed as true helices, and the external location of the passages 224 still facilitates manufacturability, for example, as compared with internal helical passages, such as by enabling molding with a simple open-close mold with no complex actions involving cams or other complex mechanical linkages.

The insert guide member 212 can comprise any suitable material that is sufficiently resilient to deform with articulation of the wrist 105 (FIG. 1) yet exhibits sufficient tensile and compressive strength to withstand the forces placed on it by articulation of the wrist 105 and the actuation member 108 (FIG. 1) (e.g., by actuation of the end effector 106). Suitable materials can include silicone rubbers, composites of thermoplastics, machinable plastics, and other materials. Such materials can also be chosen for their manufacturability, such as ability to be injection molded, machined, etc. Further, the insert guide member 212 can be manufactured using any other appropriate process, such as additive manufacturing, casting, or other methods.

Instruments including the embodiments described herein may be used, for example, with remotely operated, computer-assisted surgical systems employing robotic technology such as, for example, with a DA VINCI® Surgical System, such as the DA VINCI SI® Surgical System or the DA VINCI XI® Surgical System, Da Vinci SP, and Ion, both with or without Single-Site® single orifice surgery technology, all commercialized by Intuitive Surgical, Inc. of Sunnyvale, California Although various embodiments described herein are discussed with regard to surgical instruments used with a manipulating system of a computer-assisted surgical system employing robotic technology, the present disclosure is not limited to use with surgical instruments for such surgical systems. For example, various embodiments described herein can optionally be used in conjunction with hand-held, manual or semi-automated surgical instruments, such as those used for manual laparoscopic surgery, or other surgical and non-surgical instruments.

As discussed above, in accordance with various embodiments, surgical instruments of the present disclosure are configured for use in teleoperated, computer-assisted surgical systems employing robotic technology (sometimes referred to as robotic surgical systems). Referring now to FIG. 5, an embodiment of a manipulating system 500 of a computer-assisted surgical system, to which surgical instruments are configured to be mounted for use, is shown. Such a surgical system may further include a user control system, such as a surgeon console (not shown) for receiving input from a user to control instruments coupled to the manipulating system 500, as well as an auxiliary system, such as auxiliary systems associated with the DA VINCI SI® and DA VINCI XI®, Da Vinci SP, and Ion systems noted above.

As shown in the embodiment of FIG. 5, a manipulating system 500 includes a base 520, a main column 540, and a main boom 560 connected to main column 540. Manipulating system 500 also includes a plurality of manipulator arms 510, 511, 512, 513, which are each connected to main boom 560. Manipulator arms 510, 511, 512, 513 each include an instrument mount portion 522 to which an instrument 530 may be mounted, which is illustrated as being attached to arm 510. Portions of manipulator arms 510, 511, 512, 513 may be manipulated during a surgical procedure according to commands provided by a user at the surgeon console. In an embodiment, signal(s) or input(s) transmitted from a surgeon console are transmitted to the control/vision cart, which may interpret the input(s) and generate command(s) or output(s) to be transmitted to the manipulating system 500 to cause manipulation of the instrument 530 (only one such instrument being mounted in FIG. 5) and/or portions of arm 510 to which the instrument 530 is coupled at the manipulating system 500.

Instrument mount portion 522 comprises a drive assembly 523 and a cannula mount 524, with a force transmission mechanism 534 (which may generally correspond to the force transmission mechanism 102 discussed in connection with FIG. 1) of the instrument 530 connecting with the drive assembly 523, according to an embodiment. Cannula mount 524 is configured to hold a cannula 536 through which a shaft 532 of instrument 530 may extend to a surgery site during a surgical procedure. drive assembly 523 contains a variety of drive and other mechanisms that are controlled to respond to input commands at the surgeon console and transmit forces to the force transmission mechanism 534 to actuate the instrument 530, as those skilled in the art are familiar with.

Although the embodiment of FIG. 5 shows an instrument 530 attached to only manipulator arm 510 for ease of viewing, an instrument may be attached to any and each of manipulator arms 510, 511, 512, 513. An instrument 530 may be a surgical instrument with an end effector as discussed herein. A surgical instrument with an end effector may be attached to and used with any of manipulator arms 510, 511, 512, 513.

Other configurations of surgical systems, such as surgical systems configured for single-port surgery, are also contemplated. For example, with reference now to FIG. 6, a portion of an embodiment of a manipulator arm 2140 of a manipulating system with two surgical instruments 2300, 2310 in an installed position is shown. The surgical instruments 2300, 2310 can generally correspond to instruments discussed above, such as instrument 100 disclosed in connection with FIG. 1. For example, the embodiments described herein may be used with a DA VINCI SP® Surgical System, commercialized by Intuitive Surgical, Inc. of Sunnyvale, California. The schematic illustration of FIG. 6 depicts only two surgical instruments for simplicity, but more than two surgical instruments may be mounted in an installed position at a manipulating system as those having ordinary skill in the art are familiar with. Each surgical instrument 2300, 2310 includes a shaft 2320, 2330 that at a distal end has a moveable end effector or an endoscope, camera, or other sensing device, and may or may not include a wrist mechanism (not shown) to control the movement of the distal end.

In the embodiment of FIG. 6, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site.

Other configurations of manipulating systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 2385, 2390 (which may generally correspond to force transmission mechanism 102 disclosed in connection with FIG. 1) are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate surgical instruments 2300, 2310.

The embodiments described herein are not limited to the embodiments of FIG. 5 and FIG. 6, and various other teleoperated, computer-assisted surgical system configurations may be used with the embodiments described herein. The diameter or diameters of an instrument shaft, wrist mechanism, and end effector are generally selected according to the size of the cannula with which the instrument will be used and depending on the surgical procedures being performed.

In various exemplary embodiments described and shown herein, the flux conduits comprise electrical conductors. However, the present disclosure is not intended to be limiting and contemplates other flux conduits, such as tubing for transmitting light, gasses, liquids, vacuum, and other types of fluxes. Moreover, while the various exemplary embodiments described and shown herein include two electrical conductors received respectively in two passages of the insert guide member, the present disclosure contemplates other numbers of flux conduits and corresponding passages, such as one or more than two. In addition, while the instrument as disclosed herein can include articulating joints that can articulate about pivot axes, other types of joints, such as flexible joints generally bendable relative to the shaft without a defined pivoting axis, are within the scope of the present disclosure.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A surgical instrument, comprising:
    a shaft;
    an end effector;
    a wrist coupling the end effector to the shaft, the wrist having a central channel extending along a length of the wrist; and
    an insert guide member positioned in the central channel, the insert guide member comprising:
        an exterior lateral wall extending between a first end and a second end of the insert guide member;
        an interior lateral wall extending between the first end and the second end, the interior lateral wall defining a bore extending from the first end to the second end;
        a longitudinal axis extending along the bore; and
        two passages defined on opposite sides of the longitudinal axis, each passage having a length extending from the first end of the insert guide member to the second end of the insert guide member,
        wherein a first portion of the length of each passage extends along the insert guide member between the interior lateral wall of the insert guide member and the exterior lateral wall of the insert guide member,
        wherein a second portion of the length of each passage extends along the insert guide member and opens radially outwardly to the exterior lateral wall of the insert guide member, and
        wherein, in a cross-section taken perpendicular to the longitudinal axis of the insert guide member, the second portion of the length of each passage is elongate along a direction transverse to a radial direction of the insert guide member and perpendicular to the longitudinal axis of the passage.

2. The surgical instrument of claim 1, wherein the second portion of the length of each passage exhibits an angular displacement along at least a portion of a length of the insert guide member about the longitudinal axis of the insert guide member.

3. The surgical instrument of claim 2, wherein the second portion of the length of each passage follows a non-helical path along the portion of the length of the insert guide member.

4. The surgical instrument of claim 1, wherein the first portion of the length of each passage is parallel to the longitudinal axis of the insert guide member.

5. The surgical instrument of claim 1, wherein the bore of the insert guide member is concentric with the longitudinal axis of the insert guide member.

6. The surgical instrument of claim 5, wherein the first portion and second portion of each passage are radially offset from the bore of the insert guide member.

7. The surgical instrument of claim 1, further comprising an actuation member received in the bore of the insert guide member and operably coupled to actuate the end effector.

8. The surgical instrument of claim 1, further comprising at least one flux conduit received in each passage.

9. The surgical instrument of claim 8, wherein the at least one flux conduit is operably coupled to the end effector.

10. The surgical instrument of claim 8, wherein the flux conduit comprises one of an electrical conductor, a hollow tube, and an optical fiber.

11. The surgical instrument of claim 10, wherein the end effector comprises an electrode configured to deliver electrosurgical energy.

12. The surgical instrument of claim 1, wherein the end effector comprises opposing jaw members.

13. The surgical instrument of claim 1, wherein the insert guide member comprises:
    a proximal portion extending at least partially within the shaft;
    a distal portion extending at least partially within a component of the end effector; and
    an intermediate portion between the proximal portion and the distal portion.

14. The surgical instrument of claim 13, wherein the intermediate portion extends at least partially within the wrist.

15. The surgical instrument of claim 13, wherein the proximal portion, intermediate portion, and distal portion are formed as a single component.

16. The surgical instrument of claim 13, wherein the proximal portion and distal portion have a diameter larger than a diameter of the intermediate portion.

17. The surgical instrument of claim 1, wherein the wrist comprises two or more joints.

18. The surgical instrument of claim 17, wherein the two or more joints comprise articulation axes oriented along different directions.

19. The surgical instrument of claim 17, wherein the two or more joints comprise articulation axes orthogonal to one another.

20. The surgical instrument of claim 1, wherein the cross-section of the second portion of the insert guide member taken perpendicular to the longitudinal axis is non-symmetrical about a line intersecting and perpendicular to the longitudinal axis.

* * * * *